United States Patent [19]
Jung et al.

[11] Patent Number: 5,854,363
[45] Date of Patent: Dec. 29, 1998

[54] (OMEGA-ALKENYL) (CYCLOPENTACARBYL) METALLOCENE COMPOUNDS

[75] Inventors: Michael Jung; Helmut G. Alt, both of Bayreuth, Germany; M. Bruce Welch, Bartlesville, Okla.

[73] Assignee: Phillips Petroleum Company, Bartlesville, Okla.

[21] Appl. No.: 980,696

[22] Filed: Nov. 24, 1997

Related U.S. Application Data

[63] Continuation of Ser. No. 781,157, Jan. 8, 1997, abandoned.

[51] Int. Cl.$^6$ ............ C08F 4/44; C08F 110/02; C07F 17/00
[52] U.S. Cl. ............ 526/160; 556/1; 556/43; 556/53; 556/54; 556/58; 556/103; 556/117; 534/10; 534/15; 526/164; 526/169; 526/335; 526/336; 526/352; 526/943; 502/103; 502/117
[58] Field of Search ............ 556/1, 43, 53, 556/54, 58, 103, 117; 534/10, 15; 526/160, 164, 169, 335, 336, 352, 943; 502/103, 117

[56] References Cited

U.S. PATENT DOCUMENTS

| | | | |
|---|---|---|---|
| 5,169,818 | 12/1992 | Antberg et al. | 502/159 |
| 5,191,132 | 3/1993 | Patsidis et al. | 585/375 |
| 5,391,789 | 2/1995 | Rohrmann | 556/11 |
| 5,393,911 | 2/1995 | Patsidis et al. | 556/489 |
| 5,406,013 | 4/1995 | Patsidis et al. | 585/375 |
| 5,436,305 | 7/1995 | Alt et al. | 526/160 |
| 5,498,581 | 3/1996 | Welch et al. | 402/102 |
| 5,565,592 | 10/1996 | Patsidis et al. | 556/11 |

FOREIGN PATENT DOCUMENTS

| | | |
|---|---|---|
| 0 586 167 A1 | 3/1994 | European Pat. Off. . |
| 0 604 908 A2 | 7/1994 | European Pat. Off. . |

*Primary Examiner*—Porfirio Nazario-Gonzalez
*Attorney, Agent, or Firm*—Carl D. Corvin

[57] ABSTRACT

An (omega-alkenyl) (cyclopentacarbyl) metallocene compound is provided. Polymerization processes therewith are also provided.

40 Claims, No Drawings

(OMEGA-ALKENYL) (CYCLOPENTACARBYL) METALLOCENE COMPOUNDS

This application is a File Wrapper continuation of application Ser. No. 08/781,157, filed Jan. 8, 1997 now abandoned.

BACKGROUND OF THE INVENTION

In general, this invention is related to the fields of (omega-alkenyl) (cyclopentacarbyl) metallocene compounds and processes that use (omega-alkenyl) (cyclopentacarbyl) metallocene compounds.

The production of polymers that comprise ethylene is a multi-billion dollar enterprise. Many different catalysts can be used to polymerize ethylene. However, very few of these catalysts are of commercial importance. Currently, millions of dollars have been spent on research to make metallocene catalysts more commercially viable and thus, more commercially important. This is because the polymers produced by such metallocene catalysts have properties that currently no other single polymer can reproduce. However, one of the technical problems associated with these metallocene catalysts is that they are homogenous with the polymerization medium. That is, they are soluble in the medium in which the polymerization is conducted. This is a drawback to the use of such metallocene catalysts because most commercially important polymerization processes use heterogenous catalysts. Therefore, in order to make metallocene catalysts more commercially important, heterogenous metallocene catalysts must be produced.

Additionally, it is very important to have a metallocene catalyst that has high activity. That is, a metallocene catalyst that produces a significant amount of polymer per unit of time is highly desirable.

SUMMARY OF THE INVENTION

An object of this invention is to provide an (omega-alkenyl) (cyclopentacarbyl) metallocene compound.

Another object of this invention is to provide a process to polymerize olefins, especially ethylene, with an (omega-alkenyl) (cyclopentacarbyl) metallocene compound.

In accordance with one embodiment of this invention an (omega-alkenyl) (cyclopentacarbyl) metallocene compound is provided.

In accordance with another embodiment of this invention a process to polymerize olefins, especially ethylene, with an (omega-alkenyl) (cyclopentacarbyl) metallocene compound is provided. This process comprises (or optionally consists essentially of, or consists of): using an (omega-alkenyl) (cyclopentacarbyl) metallocene compound to polymerize monomers into polymers.

The objects and advantages of this invention are further described and defined in the following description and claims. It should be noted that the invention described herein can be practiced without any components or steps not specifically detailed herein.

DETAILED DESCRIPTION OF THE INVENTION

In general, (omega-alkenyl) (cyclopentacarbyl) metallocene compounds are those compounds having the general formula indicated in Box One.

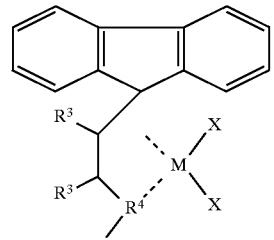

BOX ONE
GENERAL FORMULA FOR
(OMEGA-ALKENYL)(CYCLOPENTACARBYL)
METALLOCENE COMPOUNDS

In this general formula, R is an $(R^1)_2C=C(R^1)-(C(R^1)_2)_n-C(R^1)_2-$ group (where n is from 0 to about 20). In this group, each $R^1$ can be any substituent that does not substantially, and adversely, interfere with any of the processes disclosed herein. For example, each $R^1$ can be a hydrocarbyl having from 1 to about 20 carbon atoms. However, it is preferred that each $R^1$ have from 1 to 10 carbon atoms, and it is even more preferred that each $R^1$ have from 1 to 6 carbon atoms. Further examples of $R^1$ are hydrogen, alkyl, aryl, alkoxy, and aryloxy. Currently, it is most preferred if $R^1$ is hydrogen.

The R group is attached to a cyclopentacarbyl group ($R^4$ in Formula One) which can be either substituted or unsubstituted, and which can form a metallocene compound with a transition metal. The substituents of the cyclopentacarbyl group can be any substituent that does not substantially, and adversely, interfere with any of the processes disclosed herein. Examples of cyclopentacarbyl groups are substituted and unsubstituted cyclopentadiene groups and substituted and unsubstituted indenyl groups. Currently it is preferred if the cyclopentacarbyl group ($R^4$) is an indenyl.

The cyclopentacarbyl group is attached to an ethane bridging group that can be substituted or unsubstituted. The substituents ($R^3$) of the ethane bridging group can be any substituent that does not substantially, and adversely, interfere with any of the processes disclosed herein. Examples of such substituents are hydrogen, alkyl, aryl, alkoxy, and aryloxy. Currently, it is preferred if each $R^3$ is hydrogen.

The fluorenyl group in the general formula can be substituted or unsubstituted. The substituents of the fluorenyl group can be any substituent that does not substantially, and adversely, interfere with any of the processes disclosed herein. Examples of such substituents are hydrogen, alkyl, aryl, alkoxy, and aryloxy. Currently, it is preferred if the substituents are hydrogen.

In the general formula, M is a transition metal selected from the group consisting of titanium, zirconium, hafnium, vanadium, niobium, tantalum, chromium, molybdenum, tungsten, and the lanthanides. Currently, the preferred transition metals are zirconium and hafnium, however, zirconium is most preferred.

In the general formula, X is a alkyl, aryl, alkoxy, aryloxy, amides, hydride, or halogen. Currently, it is most preferred if X is a halogen. However, it is most preferred if X is chlorine.

This (omega-alkenyl) (cyclopentacarbyl) metallocene compound can be produced by first taking a cyclopentacarbyl compound and reacting it with a organometal compound such as, for example, n-butyllithium, to form a cyclopentacarbyl metal compound. In general, the metal in the organometal compound is any Group I metal and the organo part of the compound is an alkyl. The cyclopentacarbyl compound is any compound that has at least five carbon atoms arranged in a cyclic structure. This cyclopentacarbyl compound can be either substituted or unsubstituted. Additionally, this cyclopentacarbyl compound can form a metallocene compound with a transition metal. The substituents of the cyclopentacarbyl compound can be any substituent that does not substantially, and adversely, interfere with any of the processes disclosed herein. Examples of cyclopentacarbyl compounds are substituted and unsubstituted cyclopentadiene groups and substituted and unsubstituted indenyl groups. In general, the reaction of the cyclopentacarbyl compound with an organometal compound to produce a cyclopentacarbyl metal is conducted at any suitable temperature and pressure. Currently, a temperature of about −80° C. to about 160° C. and a pressure of about 0 to about 100 atmospheres are preferred. However, a temperature of about −80° C. to about 60° C. and a pressure of about 1 atmosphere are more preferred. The molar ratio of cyclopentacarbyl compound to the organometal compound can be any suitable ratio. Currently, molar ratios from 1 to 1 are preferred.

This cyclopentacarbyl metal compound is then reacted with a haloalkene to produce an (omega-alkenyl) cyclopentacarbyl compound. In general, the reaction of the cyclopentacarbyl metal compound with a haloalkene to produce an (omega-alkenyl) cyclopentacarbyl compound is conducted at any suitable temperature and pressure. Currently, a temperature of about −80° C. to about 160° C. and a pressure of about 0 to about 100 atmospheres are preferred. However, a temperature of about −80° C. to about 60° C. and a pressure of about 1 atmosphere are more preferred. The molar ratio of cyclopentacarbyl metal compound to the haloalkene can be any suitable ratio. Currently, molar ratios from 1 to 1 are preferred.

Once the (omega-alkenyl) cyclopentacarbyl compound is produced it can be used to produce metallocene compounds wherein the (omega-alkenyl) cyclopentacarbyl compound is, at least, one of the ligands of the metallocene compound.

Various methods are known in the art to bind a ligand to a transition metal in order to produce a metallocene compound. For example, the following references can be consulted: U.S. Pat. Nos. 5,436,305; 5,498,581; 5,565,592; and European Application 524,624 (the entire disclosures of which are hereby incorporated by reference). In general, however, metallocene compounds that contain an (omega-alkenyl) (cyclopentacarbyl) compound can be prepared by reacting the (omega-alkenyl) (cyclopentacarbyl) compound with an alkali metal alkyl compound to produce a ligand salt that is then reacted with a transition metal compound to yield a metallocene compound.

These metallocene compounds can be used to polymerize various olefins. The particular polymerization conditions employed using these compounds can vary depending upon the particular results desired. Usually these compounds are used with organoaluminoxane compounds, such as, for example, methylaluminoxane, to form better polymerization catalysts. The ratio of the transition metal to the organoaluminoxane composition can vary widely depending upon the particular composition selected and the results desired. Typically, the atomic ratio of aluminum in the organoaluminoxane composition to the transition metal is in the range of about 1/1 to about 20000/1, preferably about 15/1 to about 5000/1, and more preferably about 100/1 to about 1000/1.

Examples of some monomers for polymerization include ethylene and alpha-olefins having 3 to 20 carbon atoms, such as propylene, 1-butene, 3-methyl-1-butene, 3-methyl-1-pentene, 3 ethylene-1-hexene, 1-hexene, 4-methyl-1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, catalyst, and diluent, if employed, are continuously added to the reactor as needed and polymer product is continuously or at least periodically removed. Generally, in such processes, ethylene is polymerized in the presence of a suitable liquid diluent, a higher alpha-olefin comonomer, and optionally, hydrogen. The polymerization temperature can vary over the range which will allow for slurry polymerization. Often slurry polymerization will be conducted at a temperature in the range of about 50° C. to about 100° C., although higher and lower temperatures can be used.

One of the benefits of this invention is that during polymerization the metallocene compound is incorporated into the polymer chain thereby forming a heterogenous metallocene catalyst. As discussed above, this is a very important result because it increases the commercial importance of metallocene compounds. For example, a heterogenous metallocene catalyst can be formed by prepolymerizing these metallocene compounds with a monomer, such as, for example, ethylene, to form a prepolymer supported metallocene compound. Examples of such techniques are disclosed in U.S. Pat. No. 5,498,581, the entire disclosure of which is hereby incorporated by reference.

The following examples are provided to further illustrate this invention. However, the invention should not be construed to be limited to the particular embodiments in these examples.

EXAMPLES

All examples were carried out using standard Schlenk techniques with the exclusion of oxygen and air moisture under argon. The solvents were dried over either: (a) Na/K alloy for ether, hexane, pentane, tetrahydrofuran, and toluene; (b) $P_4O_{10}$ for methylene chloride; or (c) magnesium for methanol; and then distilled under argon.

Example One

Preparation of an (Omega-Alkenyl) Cyclopentacarbyl Compound

Example 1-1

Ten mL (85.7 mmol) of indene, which is a cyclopentacarbyl compound, was added to a container that contained 150 mL of diethyl ether and 15 mL of tetrahydrofuran to form a first mixture. This first mixture was then reacted with 53.6 mL (85.7 mmol) of n-butyllithium (1.6M in hexane) to form indenyllithium, which is a cyclopentacarbyl metal compound. This reaction took place at −78° C. A yellow solution was formed. This yellow solution was then stirred at room temperature (about 25° C.) for four hours and then cooled again to −78° C. An equivalent quantity of 1-bromopropene, a haloalkene compound, was added dropwise to the yellow solution to form a second mixture. This second mixture was then stirred overnight at room temperature (about 25° C.). Thereafter, this second mixture was then hydrolyzed with 50 mL of water to form an organic phase and a water phase. The organic phase was dried over sodium sulfate and then the solvent was evaporated under a vacuum to produce a third mixture. This third mixture was then distilled using a high vacuum ($10^{-2}$ torr) to obtain a product. The product obtained was allyl-1-indene, which is an (omega-alkenyl) cyclopentacarbyl compound.

Example 1-2

Ten mL (85.7 mmol) of indene, which is a cyclopentacarbyl compound, was added to a container that contained 150 mL of diethyl ether and 15 mL of tetrahydrofuran to form a first mixture. This first mixture was then reacted with 53.6 mL (85.7 mmol) of n-butyllithium (1.6M in hexane) to form indenyllithium, which is a cyclopentacarbyl metal compound. This reaction took place at −78° C. A yellow solution was formed. This yellow solution was then stirred at room temperature (about 25° C.) for four hours and then cooled again to −78° C. An equivalent quantity of 1-bromohexene, a haloalkene compound, was added dropwise to the yellow solution to form a second mixture. This second mixture was then stirred overnight at room temperature (about 25° C.). Thereafter, this second mixture was then hydrolyzed with 50 mL of water to form an organic phase and a water phase. The organic phase was dried over sodium sulfate and then the solvent was evaporated under a vacuum to produce a third mixture. This third mixture was then distilled using a high vacuum ($10^{-2}$ torr) to obtain a product. The product obtained was 5-hexenyl-1-indene, which is an (omega-alkenyl) cyclopentacarbyl compound.

Example Two

Preparation of an (Omega-Alkenyl) (Cyclopentacarbyl) Metallocene Compound

Example 2-1

Ten mmol of allyl-1-indene, prepared in Example 1-1, was mixed with 60 mL of diethyl ether and 6 mL of hexamethylphosphoric acid triamide to form a first mixture. This first mixture was then reacted with 6.25 mL of butyllithium (1.6M solution in hexane) to form a second mixture. This second mixture was stirred for four hours. Thereafter 2.73 grams (10 mmol) of(1-bromo) (2-(9-fluorenyl)) ethane, which is a (monohalogen) (cyclopentacarbyl) alkane compound, was added to the second mixture to form a third mixture. This third mixture was then stirred for three days. Thereafter, this third mixture was then hydrolyzed with water to form an organic phase and a water phase. The organic phase was then dried over sodium sulfate and thereafter evaporated to form a residue. This residue was mixed with pentane and then filtered over silica gel followed by evaporation to produce a first product. This first product was 1-(3-allyl)indenyl-2-(9-fluorenyl) ethane. One gram of this first product was mixed with 40 mL of diethyl ether to form a fourth mixture. This fourth mixture was stirred with 2 equivalents of n-butyllithium (1.6M in hexane) for about eight hours at room temperature (about 25° C.) to form a fifth mixture. Thereafter, an equivalent of zirconium tetrachloride was added to the fifth mixture and stirred overnight to form a second product. This second product was 1-(3-allyl)indenyl-2-(9-fluorenyl) ethane zirconium dichloride, a (omega-alkenyl) (cyclopentacarbyl) metallocene compound.

Example 2-2

Ten mmol of 5-hexenyl-1-indene, prepared in Example 1-2, was mixed with 60 mL of diethyl ether and 6 mL of hexamethylphosphoric acid triamide to form a first mixture. This first mixture was then reacted with 6.25 mL of butyllithium (1.6M solution in hexane) to form a second mixture. This second mixture was stirred for four hours. Thereafter 2.73 grams (10 mmol) of 1-bromo-2-(9-fluorenyl) ethane, which is a (monohalogen) (cyclopentacarbyl) alkane compound, was added to the second mixture to form a third mixture. This third mixture was stirred for three days. This third mixture was then hydrolyzed with water to form an organic phase and a water phase. The organic phase was then dried over sodium sulfate and thereafter evaporated to form a residue. This residue was mixed with pentane and then filtered over silica gel followed by evaporation to produce first product. This first product was 1-(3-hex-5-enyl)indenyl-2-(9-fluorenyl) ethane. One gram of this first product was mixed with 40 mL of diethyl ether to form a fourth mixture. This fourth mixture was stirred with 2 equivalents of n-butyllithium (1.6M in hexane) for about eight hours at room temperature (about 25° C.) to form a fifth mixture. Thereafter, an equivalent of zirconium tetrachloride was added to the fifth mixture and stirred overnight to form a second product. This second product was 1-(3-hex-5-enyl) indenyl-2-(9-fluorenyl) ethane zirconium dichloride, a metallocene compound.

Example Three

Polymerization of Ethylene with an (Omega-Alkenyl) (Cyclopentacarbyl) Metallocene Compound

Example 3-1

About 10 mg of 1-(3-allyl)indenyl-2-(9-fluorenyl) ethane zirconium dichloride, prepared in Example 2-1, was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.0 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 155 grams of polyethylene was recovered. The activity of the (omega-alkenyl) (cyclopentacarbyl) metallocene compound was about 153,000 grams polyethylene/(mmol of zirconium) (hour).

Example 3-2

About 10 mg of 1-(3-hex-5-enyl)indenyl-2-(9-fluorenyl) ethane zirconium dichloride, prepared in Example 2-2, was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.8 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 180 grams of polyethylene was recovered. The activity of this (omega-alkenyl) (cyclopentacarbyl) metallocene compound was about 198,000 grams polyethylene/ (mmol of zirconium) (hour).

Example Four

Polymerization of Ethylene with an (Omega-Alkenyl) (Cyclopentacarbyl) Metallocene Compound to Form a Heterogenous Catalyst Complex

Example 4-1

In a Schlenk tube 1-(3-allyl)indenyl-2-(9-fluorenyl) ethane zirconium dichloride, prepared in Example 2-1, was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Example 4-2

In a Schlenk tube 1-(3-hex-5-enyl)indenyl-2-(9-fluorenyl) ethane zirconium dichloride, prepared in Example 2-2, was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Comparative Example One

About 10 mg of (5-indenyl)(6-fluorenyl)-1-hexene zirconium dichloride was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.9 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 22 grams of polyethylene was recovered. The activity of the (omega-alkenyl) metallocene compound was about 11,500 grams polyethylene/(mmol of zirconium) (hour).

Comparative Example Two

About 10 mg of (7-indenyl)(6-fluorenyl)-1-octene zirconium dichloride, was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.8 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 155 grams of polyethylene was recovered. The activity of the (omega-alkenyl) metallocene compound was about 9,300 grams polyethylene/(mmol of zirconium) (hour).

DISCUSSION OF THE EXAMPLES

In Example 3-1,1-(3-allyl)indenyl-2-(9-fluorenyl) ethane zirconium dichloride was used to polymerize ethylene. In comparative Example One (5-indenyl)(6-fluorenyl)-1-hexene zirconium dichloride was used to polymerize ethylene. The main difference between these two compounds is that the former has an omega-propene group on the indenyl, whereas, the latter has an omega-butene group on the bridging ethane group. While this difference might seem minor to those unskilled in the art, the difference in activity is unexpected and unobvious. That is, the former compound polymerizes ethylene at an activity about 1200 percent greater than the latter.

In Example 3-2,1-(3-hex-5-enyl)indenyl-2-(9-fluorenyl) ethane zirconium dichloride was used to polyermize ethylene. In comparative Example One (5-indenyl)(6-fluorenyl)-1-octene zirconium dichloride was used to polymerize ethylene. The main difference between these two compounds is that the former has an omega-hexene group on the indenyl, whereas, the latter has an omega-hexene group on the bridging ethane group. While this difference might seem minor to those unskilled in the art, the difference in activity is unexpected and unobvious. That is, the former compound polymerizes ethylene at an activity about 2000 percent greater than the latter.

That which is claimed:

1. A composition of matter having the following formula

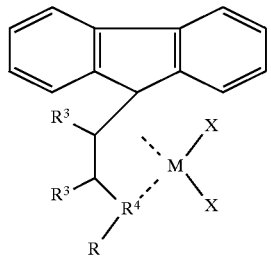

wherein M is a transition metal selected from group consisting of titanium, zirconium, hafnium, vanadium, niobium, tantalum, chromium, molybdenum, tungsten, and the lanthanides; and wherein X is a alkyl, aryl, alkoxy, aryloxy, amide, hydride, or halogen; and wherein R is an $(R^1)_2C=C(R)-(C(R^1)_2)_n-C(R^1)_2-$ group, and wherein n is from 0 to about 20, and wherein each $R^1$ can be a hydrocarbyl having from 1 to about 20 carbon atoms; and wherein $R^3$ can be hydrogen, alkyl, aryl, alkoxy, and aryloxy; and wherein $R^4$ is a cyclopentacarbyl group.

2. A composition according to claim 1 wherein M is selected from the group consisting of zirconium and hafnium.

3. A composition according to claim 1 wherein M is zirconium.

4. A composition according to claim 1 wherein X is a halogen.

5. A composition according to claim 1 wherein X is chlorine.

6. A composition according to claim 1 wherein $R^1$ has from 1 to 10 carbon atoms.

7. A composition according to claim 1 wherein $R^1$ has from 1 to 6 carbon atoms.

8. A composition according to claim 1 wherein $R^1$ is selected from the group consisting of hydrogen, alkyl, aryl, alkoxy, and aryloxy.

9. A composition according to claim 1 wherein $R^1$ is hydrogen.

10. A composition according to claim 1 wherein $R^3$ is hydrogen.

11. A composition according to claim 1 wherein $R^4$ is selected from the group consisting of substituted and unsubstituted cyclopentadiene groups.

12. A composition according to claim 1 wherein $R^4$ is selected from the group consisting of substituted and unsubstituted indenyl groups.

13. A composition of matter having the following formula

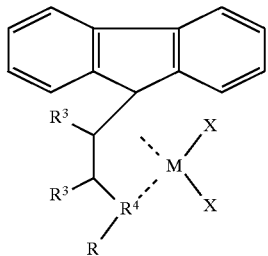

wherein M is zirconium; and wherein X is chlorine; and wherein R is an $(R^1)_2C=C(R^1)-(C(R^1)_2)_n-C(R^1)_2-$ group, and wherein n is from 0 to about 20, and wherein each $R^1$ is hydrogen; and wherein $R^3$ is hydrogen; and wherein $R^4$ is selected from the group consisting of substituted and unsubstituted indenyl groups.

14. A process of using a composition of matter having the following formula

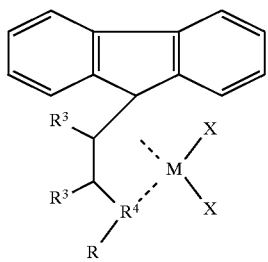

wherein M is a transition metal selected from group consisting of titanium, zirconium, hafnium, vanadium, niobium, tantalum, chromium, molybdenum, tungsten, and the lanthanides; and wherein X is a alkyl, aryl, alkoxy, aryloxy, amide, hydride, or halogen; and wherein R is an $(R^1)_2C=C(R^1)-(C(R^1)_2)_n-C(R^1)_2-$ group, and wherein n is from 0 to about 20, and wherein each $R^1$ can be a hydrocarbyl having from 1 to about 20 carbon atoms; and wherein $R^3$ can be hydrogen, alkyl, aryl, alkoxy, and aryloxy; and wherein $R^4$ is a cyclopentacarbyl group;

as a catalyst to polymerize monomers into polymers.

15. A process according to claim 14 wherein M is selected from the group consisting of zirconium and hafnium.

16. A process according to claim 14 wherein M is zirconium.

17. A process according to claim 14 wherein X is a halogen.

18. A process according to claim 14 wherein X is chlorine.

19. A process according to claim 14 wherein $R^1$ has from 1 to 10 carbon atoms.

20. A process according to claim 14 wherein $R^1$ has from 1 to 6 carbon atoms.

21. A process according to claim 14 wherein $R^1$ is selected from the group consisting of hydrogen, alkyl, aryl, alkoxy, and aryloxy.

22. A process according to claim 14 wherein $R^1$ is hydrogen.

23. A process according to claim 14 wherein $R^3$ is hydrogen.

24. A process according to claim 14 wherein $R^4$ is selected from the group consisting of substituted and unsubstituted cyclopentadiene groups.

25. A process according to claim 14 wherein $R^4$ is selected from the group consisting of substituted and unsubstituted indenyl groups.

26. A process according to claim 14 wherein said monomers comprise ethylene.

27. A process according to claim 14 wherein said monomers consist essentially of ethylene.

28. A process according to claim 14 wherein said monomers consist of ethylene.

29. A process according to claim 14 wherein said monomers comprise ethylene and olefins having 3 to 20 carbon atoms.

30. A process according to claim 14 wherein said monomers comprise ethylene and olefins selected from the group consisting of propylene, 1-butene, 3-methyl-1-butene, 3-methyl-1-pentene, 3 ethylene-1-hexene, 1-hexene, 4-methyl-1-pentene, 1-octene, 1-hexadecene, butadiene, and mixtures thereof.

31. A process according to claim 14 wherein said monomers comprise ethylene and olefins selected from the group consisting of cyclopentene, norbornene, styrene, 4-methyl styrene, vinyl cyclohexane, and mixtures thereof.

32. A process according to claim 14 wherein said monomers comprise ethylene and 1-hexene.

33. A process of using a composition of matter having the following formula

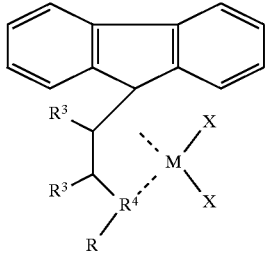

wherein M is zirconium; and wherein X is chlorine; and wherein R is an $(R^1)_2C=C(R^1)-(C(R^1)_2)_n-C(R^1)_2-$ group, and wherein n is from 0 to about 20, and wherein each $R^1$ is hydrogen; and wherein $R^3$ is hydrogen; and wherein $R^4$ is selected from the group consisting of substituted and unsubstituted indenyl groups as a catalyst to polymerize monomers into polymers.

34. A process, according to claim 33 wherein said monomers comprise ethylene.

35. A process according to claim 33 wherein said monomers consist essentially of ethylene.

36. A process according to claim 33 wherein said monomers consist of ethylene.

37. A process according to claim 33 wherein said monomers comprise ethylene and olefins having 3 to 20 carbon atoms.

38. A process according to claim 33 wherein said monomers comprise ethylene and olefins selected from the group consisting of propylene, 1-butene, 3-methyl-1-butene, 3-methyl-1-pentene, 3 ethylene-1-hexene, 1-hexene, 4-methyl-1-pentene, 1-octene, 1-hexadecene, butadiene, and mixtures thereof.

39. A process according to claim 33 wherein said monomers comprise ethylene and olefins selected from the group consisting of cyclopentene, norbornene, styrene, 4-methyl styrene, vinyl cyclohexane, and mixtures thereof.

40. A process according to claim 33 wherein said monomers comprise ethylene and 1-hexene.

* * * * *

UNITED STATES PATENT AND TRADEMARK OFFICE
CERTIFICATE OF CORRECTION

PATENT NO.    : 5,854,363

DATED         : December 29, 1998

INVENTOR(S)   : Michael Jung; Helmut G. Alt and M. Bruce Welch

It is certified that error appears in the above-identified patent and that said Letters Patent is hereby corrected as shown below:

Column 8 Line 41, please delete C(R) and insert therefore --- $C(R^1)$ ---

Signed and Sealed this

First Day of June, 1999

*Attest:*

Q. TODD DICKINSON

*Attesting Officer*    *Acting Commissioner of Patents and Trademarks*